US008315822B2

(12) United States Patent
Berme et al.

(10) Patent No.: US 8,315,822 B2
(45) Date of Patent: *Nov. 20, 2012

(54) FORCE MEASUREMENT SYSTEM HAVING INERTIAL COMPENSATION

(75) Inventors: Necip Berme, Worthington, OH (US); Hasan Cenk Guler, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 53 days.

This patent is subject to a terminal disclaimer.

(21) Appl. No.: 13/091,060

(22) Filed: Apr. 20, 2011

(65) Prior Publication Data

US 2012/0271565 A1    Oct. 25, 2012

(51) Int. Cl.
*G01G 23/01*    (2006.01)
(52) U.S. Cl. ............. 702/41; 702/87; 702/101; 702/173
(58) Field of Classification Search ............... 702/41, 702/42, 87, 101, 102, 141, 174, 173; 600/592
See application file for complete search history.

(56) References Cited

U.S. PATENT DOCUMENTS

| 3,890,958 | A | * | 6/1975 | Fister et al. ................... 600/527 |
| 4,283,764 | A | | 8/1981 | Crum et al. |
| 4,548,289 | A | * | 10/1985 | Mechling ...................... 600/587 |
| 4,830,021 | A | * | 5/1989 | Thornton ...................... 600/520 |
| 4,991,446 | A | | 2/1991 | Bechtel |
| 5,009,111 | A | | 4/1991 | West et al. |
| 5,488,203 | A | | 1/1996 | Hassel et al. |
| 5,562,572 | A | * | 10/1996 | Carmein ......................... 482/4 |
| 5,563,632 | A | | 10/1996 | Roberts |
| 5,750,937 | A | * | 5/1998 | Johnson et al. ............ 177/25.11 |
| 6,038,488 | A | | 3/2000 | Barnes et al. |
| 6,052,114 | A | | 4/2000 | Morifuji |
| 6,098,025 | A | * | 8/2000 | Bae ................................ 702/94 |
| 6,113,237 | A | | 9/2000 | Ober et al. |

(Continued)

FOREIGN PATENT DOCUMENTS

CA    2018618 C    4/1991

(Continued)

OTHER PUBLICATIONS

Pagnacco, Guido et al., Inertially Compensated Force Plate: A Means for Quantifying Subject's Ground Reaction Forces in Non-Inertial Conditions, Biomedical Sciences Instrumentation, 2000, vol. 36, pp. 397-402.*

(Continued)

*Primary Examiner* — Jeffrey R West
(74) *Attorney, Agent, or Firm* — The Law Office of Patrick F. O'Reilly III, LLC

(57) ABSTRACT

A force measurement system having inertial compensation includes a force measurement assembly with at least one accelerometer configured to measure the acceleration thereof. According to one aspect of the invention, the force measurement system additionally includes at least one angular velocity sensor configured to measure the angular velocity of the force measurement assembly. According to another aspect of the invention, the force measurement system additionally includes a data processing device with a computer-readable medium loaded thereon that is configured to execute a calibration procedure for determining the inertial parameters of the force measurement assembly by utilizing the measured acceleration of the force measurement assembly while the force measurement assembly is subjected to a plurality of applied linear and/or rotational motion profiles. According to still another aspect of the invention, the at least one accelerometer is disposed on the force transducer.

30 Claims, 10 Drawing Sheets

U.S. PATENT DOCUMENTS

| | | | |
|---|---|---|---|
| 6,152,564 A | 11/2000 | Ober et al. | |
| 6,162,189 A | 12/2000 | Girone et al. | |
| 6,285,358 B1 | 9/2001 | Roberts | |
| 6,295,878 B1 | 10/2001 | Berme | |
| 6,354,155 B1 | 3/2002 | Berme | |
| 6,389,883 B1 | 5/2002 | Berme et al. | |
| 6,508,132 B1 | 1/2003 | Lohr et al. | |
| 6,645,126 B1 | 11/2003 | Martin et al. | |
| 6,736,018 B2 | 5/2004 | Terada | |
| 6,738,065 B1 | 5/2004 | Even-Zohar | |
| 6,774,885 B1 | 8/2004 | Even-Zohar | |
| 6,836,744 B1 * | 12/2004 | Asphahani et al. | 702/141 |
| 6,936,016 B2 | 8/2005 | Berme et al. | |
| 7,102,621 B2 | 9/2006 | Roberts | |
| 7,331,209 B2 | 2/2008 | Saari et al. | |
| 7,931,604 B2 | 4/2011 | Even-Zohar et al. | |
| 7,955,279 B2 * | 6/2011 | Berthonnaud et al. | 600/595 |
| 8,181,541 B2 | 5/2012 | Berme | |
| 2008/0221487 A1 | 9/2008 | Even-Zohar et al. | |
| 2008/0228110 A1 * | 9/2008 | Berme | 600/595 |
| 2010/0013768 A1 * | 1/2010 | Leung | 345/163 |
| 2010/0131113 A1 | 5/2010 | Even-Zohar | |
| 2011/0277562 A1 | 11/2011 | Berme | |

FOREIGN PATENT DOCUMENTS

| | | |
|---|---|---|
| CA | 2160850 C | 6/1996 |
| CA | 2345013 C | 9/2009 |
| JP | 01303296 A | 12/1989 |
| WO | 0106208 A1 | 1/2001 |

OTHER PUBLICATIONS

Robinson, "Design, Control, and Characterization of a Sliding Linear Investigative Platform for Analyzing Lower Limb Stability (SLIP-FALLS)", IEEE Transactions on Rehabilitation Engineering, vol. 6, No. 3, Sep. 1998.*

Dixon, Michael J., Development of a Load-cell Compensation System, Experimental Mechanics, Mar. 1991, pp. 21-24.

Preuss, R. et al., A simple method to estimate force plate inertial components in a moving surface, Journal of Biomechanics, Aug. 2004, vol. 37, Issue 8, pp. 1177-1180.

Yang, Feng et al., Correction of the Inertial Effect Resulting From a Plate Moving Under Low Friction Conditions, Journal of Biomechanics, Sep. 2007, vol. 40, Issue 12, pp. 2723-2730.

First office action on the merits (Non-Final Rejection) in U.S. Appl. No. 13/173,084, mailed on Aug. 8, 2011.

Second office action on the merits (Final Rejection) in U.S. Appl. No. 13/173,084, mailed on Oct. 18, 2011.

Third office action on the merits (Non-Final Rejection) in U.S. Appl. No. 13/173,084, mailed on Jun. 21, 2012.

* cited by examiner

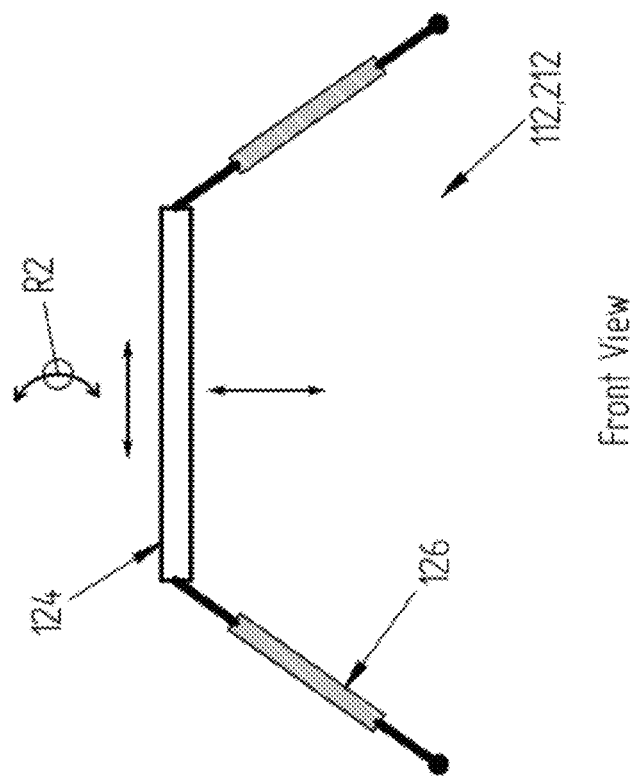
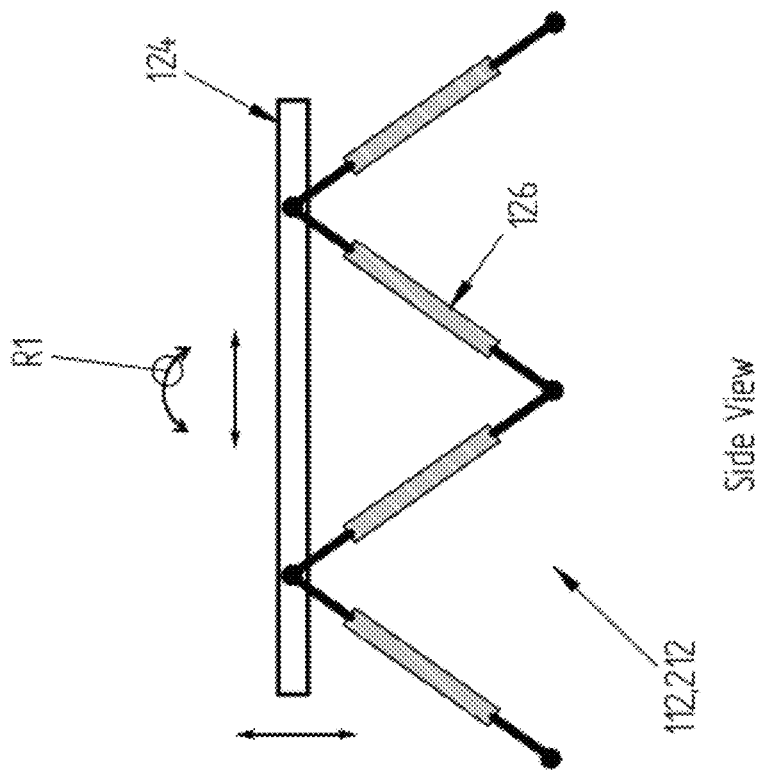

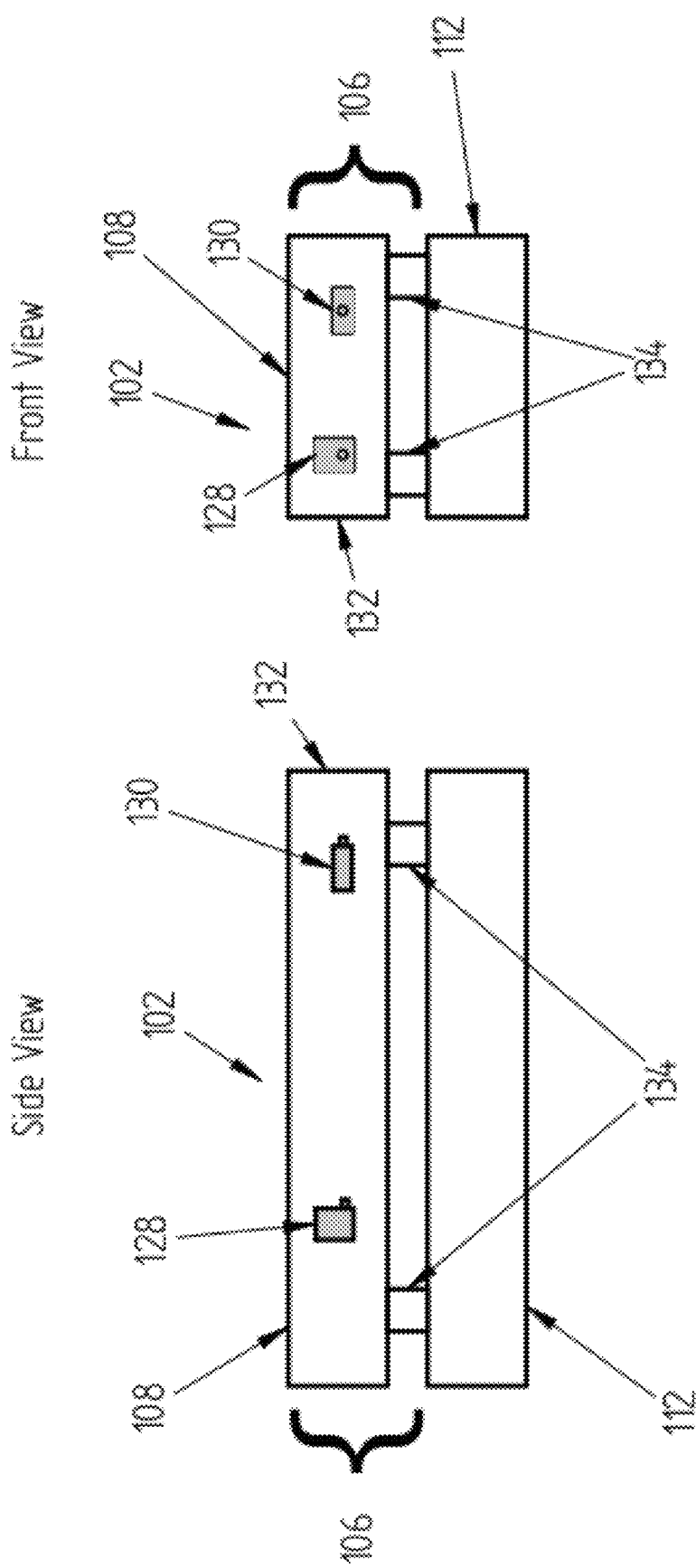

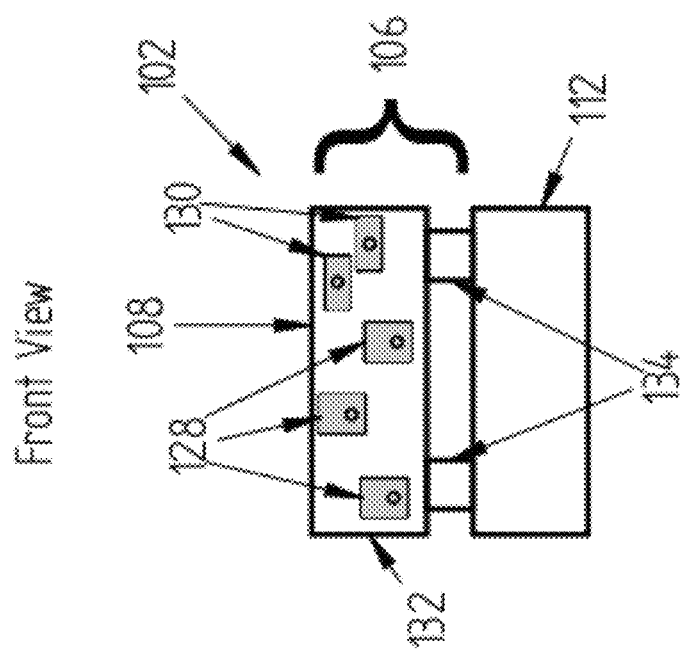
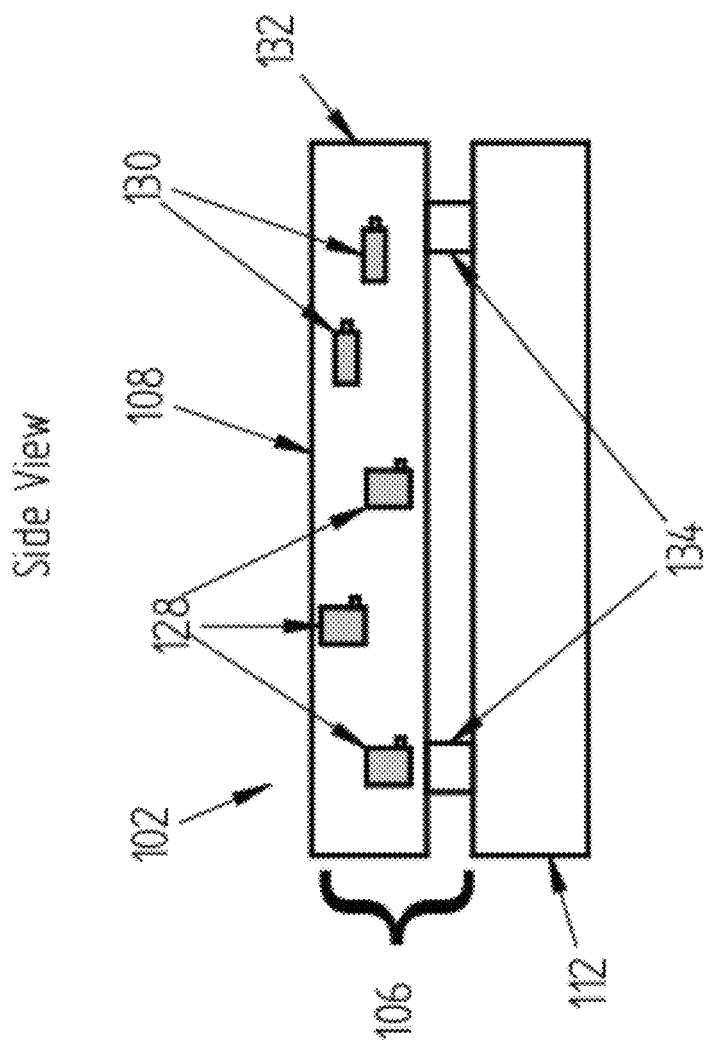

Front View

Side View

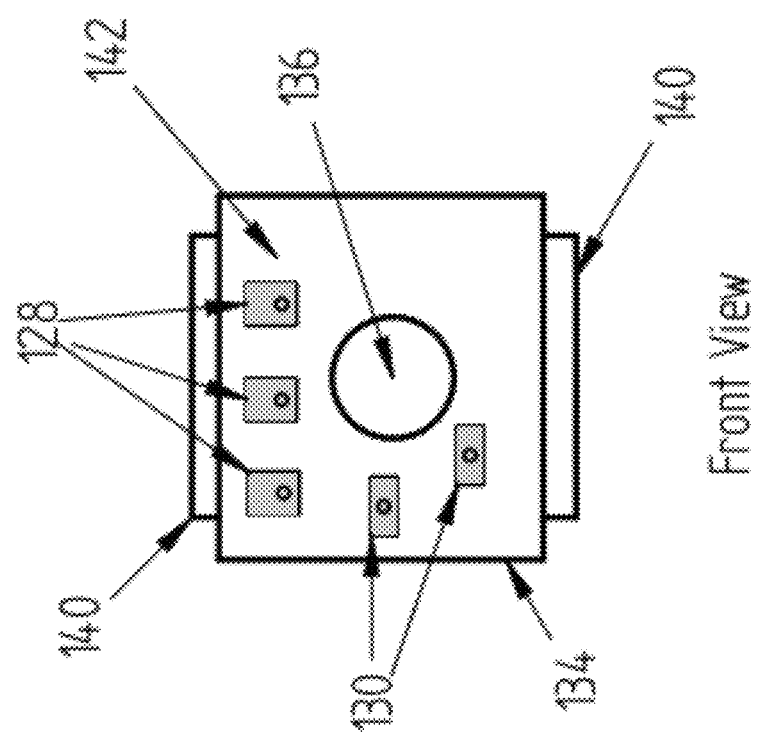
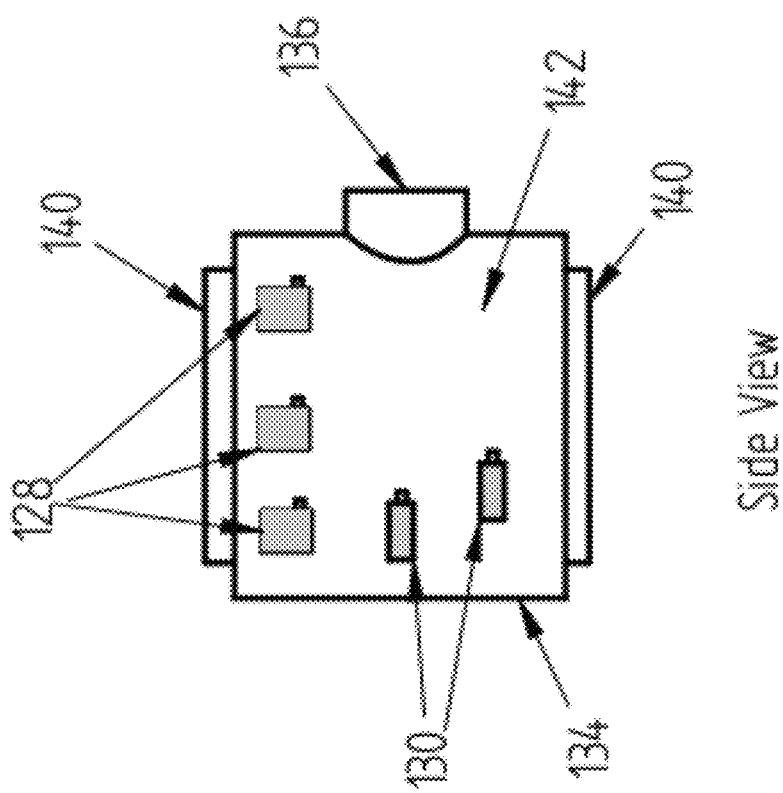
Figure 7b — Front View
Figure 7a — Side View

FORCE MEASUREMENT SYSTEM HAVING INERTIAL COMPENSATION

CROSS-REFERENCE TO RELATED APPLICATIONS

Not Applicable.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to force and/or moment measurement systems. More particularly, the invention relates to force and/or moment measurement systems with inertial compensation.

2. Description of Related Art

Force measurement systems are utilized in various fields to quantify the reaction forces and moments exchanged between a body and support surface. For example, in biomedical applications, force measurement systems are used for gait analysis, assessing balance and mobility, evaluating sports performance, and assessing ergonomics. In order to quantify the forces and moments resulting from the body disposed thereon, the force measurement assembly includes some type of force measurement device. Depending on the particular application, the force measurement device may take the form of a balance plate, force plate, jump plate, an instrumented treadmill, or some other device that is capable of quantifying the forces and moments exchanged between the body and the support surface.

Regardless of the type of force measurement device that is employed, the device is normally positioned on a support surface. In order for the device to be accurately considered as part of an inertial system, some type of rigid connection between the force measurement device and the ground on which it is placed must exist. However, in many applications, it is either impossible and/or undesirable to rigidly affix the force measurement device to the ground on which it is supported. For example, a force measurement plate used to conduct the dynamic testing of human subjects cannot be rigidly affixed to any support surface. Consequently, the force measurement assembly will move in space, and it will measure loads due to the inertia of the force measurement components in addition to the desired externally applied loads. For force measurement assemblies that have high masses, such as instrumented treadmills, these inertia forces will be comparable to, or even higher than the externally applied loads in magnitude. In such instances, it cannot be accurately assumed that the force measurement device is part of an inertial system, and it is necessary to compensate for the forces produced by the movement of the force measurement device, which results in undesirable measurement errors.

What is needed, therefore, is a force measurement system having inertial compensation that accurately corrects for the movement of the force measurement device in multiple dimensions. Moreover, a force measurement system is needed that is capable of empirically determining the inertial parameters of large, complex systems. While an analytical approach can be used for simple systems wherein the motion is limited to one direction, an analytical approach will not produce sufficiently accurate results for large systems that undergo complex multi-dimensional motion. Furthermore, a need exists for a force measurement system that produces accurate measurements when the entire system is in motion.

BRIEF SUMMARY OF THE INVENTION

Accordingly, the present invention is directed to an inertially-compensated force measurement system that substantially obviates one or more problems resulting from the limitations and deficiencies of the related art.

A first object of the present invention is to provide a force measurement system with inertial compensation that is capable of accurately compensating for the non-inertial characteristics of a large measurement system which undergoes complex motions.

A second object of the present invention is to provide a force measurement system with inertial compensation that employs a calibration procedure that is capable of accurately determining one or more inertial parameters of the system.

A third object of the present invention is to provide a force measurement system with inertial compensation that is capable of accurately determining the location of the center of gravity of a complex measurement system.

A fourth object of the present invention is to provide a force measurement system with inertial compensation that determines the inertial parameters of the force measurement system using applied motion profiles.

A fifth object of the present invention is to provide a force measurement system with inertial compensation that affords flexibility in the placement of devices that are used for inertial compensation, such as the one or more accelerometers and/or the one or more angular velocity sensors.

A sixth object of the present invention is to provide a force measurement system with inertial compensation that produces accurate measurements when the entire system is in motion.

A seventh object of the present invention is to provide a force measurement system with inertial compensation that employs an empirical approach in order to determine the inertial parameters of the system.

The aforedescribed objects are merely illustrative in nature. Additional objects and advantages of the present invention will be apparent from the following detailed description, the accompanying drawings, and the appended claims.

To achieve one or more of these objects and advantages, in accordance with a first aspect of the present invention, there is provided a force measurement system having inertial compensation, which includes: a force measurement assembly configured to receive a subject, the force measurement assembly having a surface for receiving at least one portion of the body of the subject; at least one force transducer, the at least one force transducer configured to sense a measured quantity that is representative of forces and/or moments being applied to the surface of the force measurement assembly by the subject; at least one accelerometer configured to measure the acceleration of the force measurement assembly; at least one angular velocity sensor configured to measure the angular velocity of the force measurement assembly; and a data acquisition device operatively coupled to the force measurement assembly, the data acquisition device configured to acquire the measured quantity that is representative of the forces and/or moments being applied to the surface of the force measurement assembly by the subject, the data acquisition device being further configured to acquire the acceleration and the angular velocity measured by the at least one accelerometer and the at least one angular velocity sensor, respectively, such that the acceleration and the angular velocity are capable of being used to correct an output of the force measurement system so as to provide a more accurate measurement of the forces and/or moments being applied to the surface of the force measurement assembly by the subject.

In a preferred embodiment of this aspect of the present invention, the at least one accelerometer is disposed on the force transducer or in the force transducer.

In another preferred embodiment, the at least one accelerometer is disposed on the force measurement assembly or in the force measurement assembly.

In yet another preferred embodiment, the at least one angular velocity sensor is disposed on the force transducer or in the force transducer.

In still another preferred embodiment, the at least one angular velocity sensor is disposed on the force measurement assembly or in the force measurement assembly.

In yet another preferred embodiment, the at least one force transducer comprises a plurality of force transducers for sensing measured quantities that are representative of multi-dimensional forces and/or moments being applied to the surface of the force measurement assembly by the subject. In still another preferred embodiment, the at least one accelerometer comprises a plurality of accelerometers so as to enable the multi-axis acceleration of the force measurement assembly to be determined, thereby compensating for the movement of the force measurement assembly in more than one direction.

In yet another preferred embodiment, the force measurement assembly is in the form of a force plate or platform.

In still another preferred embodiment, the force measurement assembly is in the form of an instrumented treadmill.

In yet another preferred embodiment, the force measurement system further comprises a data processing device operatively coupled to the data acquisition device, the data processing device configured to receive the measured quantity that is representative of the forces and/or moments being applied to the surface of the force measurement assembly by the subject, and to convert the measured quantity into output forces and/or moments. In this preferred embodiment, the data processing device uses the acceleration and the angular velocity measured by the at least one accelerometer and the at least one angular velocity sensor, respectively, to correct the output forces and/or moments so as to provide a more accurate measurement of the forces and/or moments being applied to the surface of the force measurement assembly by the subject.

In still another preferred embodiment, the data acquisition device further includes: a data processing device, the data processing device configured to receive the measured quantity that is representative of the forces and/or moments being applied to the surface of the force measurement assembly by the subject, and to convert the measured quantity into output forces and/or moments. In this preferred embodiment, the data processing device uses the acceleration and the angular velocity measured by the at least one accelerometer and the at least one angular velocity sensor, respectively, to correct the output forces and/or moments so as to provide a more accurate measurement of the forces and/or moments being applied to the surface of the force measurement assembly by the subject.

In yet another preferred embodiment, the data processing device includes a computer-readable medium loaded thereon that is configured to execute a calibration procedure for determining the inertial parameters of the force measurement assembly through the utilization of applied linear and/or rotational motion profiles.

In still another preferred embodiment, the inertia parameters of the force measurement system comprise the mass of the system, the rotational inertia of the system, and the position vector of the center of gravity of the system. In yet another preferred embodiment, the mass of the system, the rotational inertia of the system, and the position vector of the center of gravity of the system are mathematically determined using three-dimensional equations of motion.

In accordance with a second aspect of the present invention, there is provided a force measurement system having inertial compensation, which includes: a force measurement assembly configured to receive a subject, the force measurement assembly having a surface for receiving at least one portion of the body of the subject; at least one force transducer, the at least one force transducer configured to sense a measured quantity that is representative of forces and/or moments being applied to the surface of the force measurement assembly by the subject; at least one accelerometer configured to measure the acceleration of the force measurement assembly; and a data processing device operatively coupled to the at least one force transducer and the at least one accelerometer of the force measurement assembly, the data processing device including a computer-readable medium loaded thereon that is configured to execute a calibration procedure for determining the inertial parameters of the force measurement assembly by utilizing the measured acceleration of the force measurement assembly while the force measurement assembly is subjected to a plurality of applied linear and/or rotational motion profiles; wherein the data processing device is configured to receive the measured quantity that is representative of the forces and/or moments being applied to the surface of the force measurement assembly by the subject, and to convert the measured quantity into output forces and/or moments; and wherein the data processing device is further configured to utilize the computed inertial parameters of the force measurement assembly and the acceleration measured by the at least one accelerometer for correcting the output forces and/or moments so as to provide a more accurate measurement of the forces and/or moments being applied to the surface of the force measurement assembly by the subject.

In a preferred embodiment of this aspect of the present invention, the at least one accelerometer is disposed on the force transducer or in the force transducer.

In another preferred embodiment, the at least one accelerometer is disposed on the force measurement assembly or in the force measurement assembly.

In yet another preferred embodiment, the force measurement assembly further comprises at least one angular velocity sensor. In still another preferred embodiment, the at least one angular velocity sensor is disposed on the force transducer or in the force transducer. In yet another preferred embodiment, the at least one angular velocity sensor is disposed on the force measurement assembly or in the force measurement assembly.

In yet another preferred embodiment, the at least one force transducer comprises a plurality of force transducers for sensing measured quantities that are representative of multi-dimensional forces and/or moments being applied to the surface of the force measurement assembly by the subject. In still another preferred embodiment, the at least one accelerometer comprises a plurality of accelerometers so as to enable the multi-axis acceleration of the force measurement assembly to be determined, thereby compensating for the movement of the force measurement assembly in more than one direction.

In yet another preferred embodiment, the force measurement assembly is in the form of a force plate or platform.

In still another preferred embodiment, the force measurement assembly is in the form of an instrumented treadmill.

In accordance with a third aspect of the present invention, there is provided force measurement system having inertial compensation, which includes: a force measurement assembly configured to receive a subject, the force measurement assembly having a surface for receiving at least one portion of the body of the subject; at least one force transducer, the at least one force transducer configured to sense a measured quantity that is representative of forces and/or moments being applied to the surface of the force measurement assembly by the subject; at least one accelerometer configured to measure the acceleration of the force measurement assembly, the at least one accelerometer being disposed on the force transducer; and a data acquisition device operatively coupled to the force measurement assembly, the data acquisition device configured to acquire the measured quantity that is representative of the forces and/or moments being applied to the surface of the force measurement assembly by the subject, the data acquisition device being further configured to acquire the acceleration measured by the at least one accelerometer such that the acceleration is capable of being used to correct an output of the force measurement system so as to provide a more accurate measurement of the forces and/or moments being applied to the surface of the force measurement assembly by the subject.

In a preferred embodiment of this aspect of the present invention, the force measurement assembly further comprises at least one angular velocity sensor.

In another preferred embodiment, the at least one angular velocity sensor is disposed on the force transducer or in the force transducer.

In yet another preferred embodiment, the at least one angular velocity sensor is disposed on the force measurement assembly or in the force measurement assembly.

In still another preferred embodiment, the at least one force transducer comprises a plurality of force transducers for sensing measured quantities that are representative of multi-dimensional forces and/or moments being applied to the surface of the force measurement assembly by the subject. In yet another preferred embodiment, the at least one accelerometer comprises a plurality of accelerometers so as to enable the multi-axis acceleration of the force measurement assembly to be determined, thereby compensating for the movement of the force measurement assembly in more than one direction.

In still another preferred embodiment, the force measurement assembly is in the form of a force plate or platform.

In yet another preferred embodiment, the force measurement assembly is in the form of an instrumented treadmill.

In still another preferred embodiment, the force measurement system further comprises a data processing device operatively coupled to the data acquisition device, the data processing device configured to receive the measured quantity that is representative of the forces and/or moments being applied to the surface of the force measurement assembly by the subject, and to convert the measured quantity into output forces and/or moments. In this preferred embodiment, the data processing device uses the acceleration measured by the at least one accelerometer to correct the output forces and/or moments so as to provide a more accurate measurement of the forces and/or moments being applied to the surface of the force measurement assembly by the subject.

In yet another preferred embodiment, the data acquisition device further includes: a data processing device, the data processing device configured to receive the measured quantity that is representative of the forces and/or moments being applied to the surface of the force measurement assembly by the subject, and to convert the measured quantity into output forces and/or moments. In this preferred embodiment, the data processing device uses the acceleration measured by the at least one accelerometer to correct the output forces and/or moments so as to provide a more accurate measurement of the forces and/or moments being applied to the surface of the force measurement assembly by the subject.

It is to be understood that the foregoing objects and summary, and the following detailed description of the present invention, are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 3a is a schematic side view of a motion base according to an embodiment of the invention;

FIG. 3b is a schematic front view of a motion base according to an embodiment of the invention;

FIG. 4a is a schematic side view of a force measurement assembly with the location of an accelerometer and an angular velocity sensor depicted thereon according to an embodiment of the invention;

FIG. 4b is a schematic front view of a force measurement assembly with the location of an accelerometer and an angular velocity sensor depicted thereon according to an embodiment of the invention;

FIG. 5a is a schematic side view of a force measurement assembly with the location of a plurality of accelerometers and a plurality of angular velocity sensors depicted thereon according to an embodiment of the invention;

FIG. 5b is a schematic front view of a force measurement assembly with the location of a plurality of accelerometers and a plurality of angular velocity sensors depicted thereon according to an embodiment of the invention;

FIG. 7a is a schematic side view of a force transducer with the location of a plurality of accelerometers and a plurality of velocity sensors depicted thereon according to an embodiment of the invention;

FIG. 7b is a schematic front view of a force transducer with the location of a plurality of accelerometers and a plurality of velocity sensors depicted thereon according to an embodiment of the invention;

Throughout the figures, the same parts are always denoted using the same reference characters so that, as a general rule, they will only be described once.

DETAILED DESCRIPTION OF THE INVENTION

Figure 1:
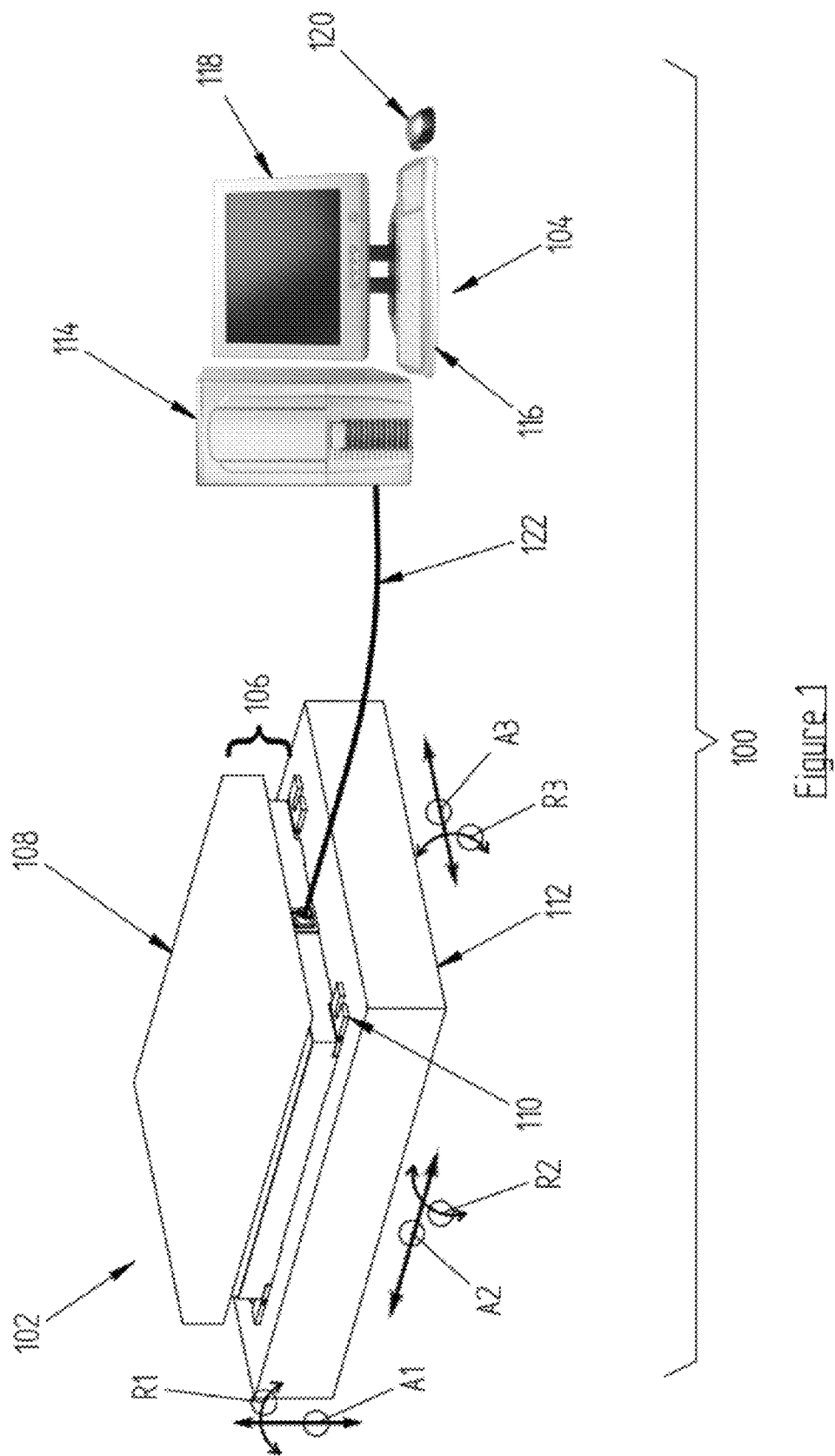
FIG. 1 is a diagrammatic perspective view of the force measurement system according to a first embodiment of the invention, wherein the force measurement assembly is in the form of a force plate or platform.

A first embodiment of the force measurement system is seen generally at 100 in FIG. 1. The force measurement system 100 generally comprises a force measurement assembly 102 operatively coupled to a data acquisition/data processing device 104 by virtue of an electrical cable 122. In the first embodiment, the force measurement assembly 102 for receiving a subject is in the form of a force plate or platform. In a preferred embodiment of the invention, the electrical cable 122 is used for data transmission, as well as for providing power to the force measurement assembly 102. Preferably, the electrical cable 122 contains a plurality of electrical wires bundled together, with at least one wire being used for power and at least another wire being used for transmitting data. The bundling of the power and data transmission wires into a single electrical cable 122 advantageously creates a simpler and more efficient design. In addition, it enhances the safety of the testing environment when human subjects are being tested on the force measurement assembly 102. However, it is to be understood that the force measurement assembly 102 can be operatively coupled to the data acquisition/data processing device 104 using other signal transmission means, such as a wireless data transmission system. If a wireless data transmission system is employed, it is preferable to provide the force measurement assembly 102 with a separate power supply in the form of an internal power supply or a dedicated external power supply.

Referring again to FIG. 1, it can be seen that the force measurement assembly 102 according to the first embodiment of the invention, includes a force plate or platform 106 that is attached to the top of a motion base 112 via a plurality of mounting brackets 110. The force plate or platform 106 has a top surface 108 that is configured to receive at least one portion of a body of a subject. In a preferred embodiment, a subject stands in an upright position atop the force plate 106 and the feet of the subject are placed on its top surface 108. In FIG. 1, the arrows A1, A2, A3 disposed adjacent to the motion base 112 schematically depict the displaceable nature of the force measurement assembly 102, which is effectuated by the motion base 112. Moreover, the curved arrows R1, R2, R3 in FIG. 1 schematically illustrate the ability of the force measurement assembly 102 to be rotated about a plurality of different axes, the rotational movement of the force measurement assembly 102 is also generated by the motion base 112.

As shown in FIG. 1, the data acquisition/data processing device 104 generally includes a central processing unit (CPU) 114 for collecting and processing the data that is received from the force measurement assembly 102, which has a plurality of peripheral devices 116-120 connected thereto. Preferably, the peripheral devices that are operatively coupled to the central processing unit 114 comprise user input devices 116, 120 in the form of a keyboard 116 and a mouse 120, as well as a graphical user interface in the form of a monitor 118. While a desktop type computing system is depicted in FIG. 1, one of ordinary skill in the art will appreciate that another type of data acquisition/data processing device 104 can be substituted for the desktop computing system such as, but not limited to, a laptop or a palmtop computing device (i.e., a PDA). In addition, rather than providing a data acquisition/data processing device 104, it is to be understood that only a data acquisition device could be provided without departing from the spirit and the scope of the claimed invention.

Figure 2:
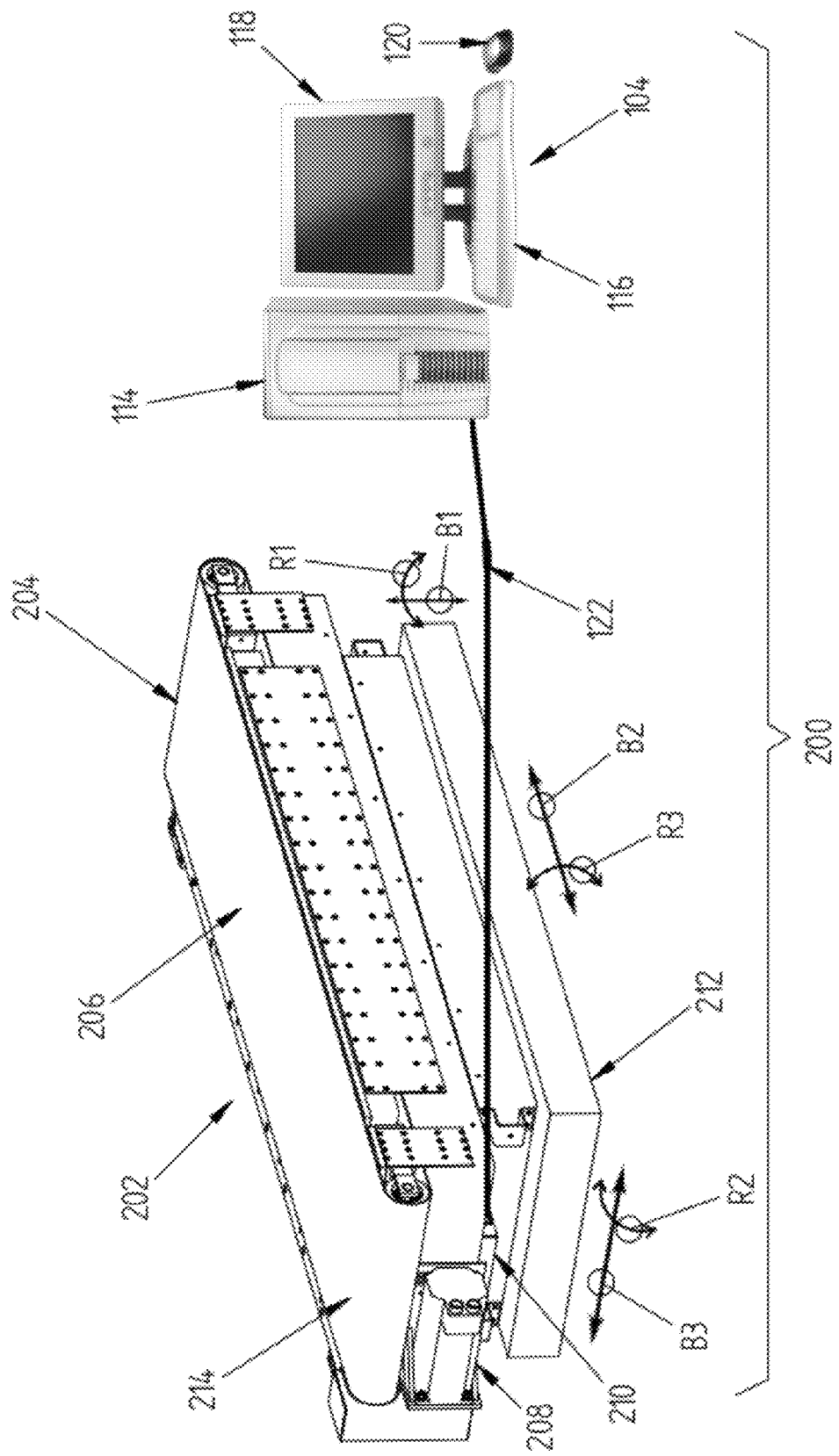
FIG. 2 is a diagrammatic perspective view of the force measurement system according to a second embodiment of the invention, wherein the force measurement assembly is in the form of an instrumented treadmill.

A second embodiment of the force measurement system is seen generally at 200 in FIG. 2. In accordance with the second embodiment of the invention, the force measurement system 200 generally comprises a force measurement assembly 202 operatively coupled to a data acquisition/data processing device 104 by virtue of an electrical cable 122. In the second embodiment, the force measurement assembly 202 for receiving a subject is in the form of an instrumented treadmill. Because the data acquisition/data processing device 104 and the electrical cable 122 are the same as that described above with regard to the first embodiment, a description of these components 104, 122 will not be repeated for this embodiment.

As illustrated in FIG. 2, the force measurement assembly 202 according to the second embodiment of the invention includes a treadmill 204 that is attached to the top of a motion base 212. The treadmill 204 has a top surface 206 that is configured to receive at least one portion of a body of a subject. In a preferred embodiment, a subject walks or runs in an upright position atop the treadmill 204 with the feet of the subject contacting the top surface 206 of the treadmill 204. The belt 214 of the treadmill 204 is rotated by an electric actuator assembly 208, which generally comprises an electric motor. The electrical cable 122 is operatively coupled to a load output device 210, which is at one end of the treadmill 204, and beneath the rotating belt 214. While it is not readily visible in FIG. 2 due to its internal location, the force measurement assembly 202, like the force measurement assembly 102, includes a force plate 106 with a plurality of force transducers disposed below the top surface 206 of the treadmill 204 so that the load being applied to the top surface 206 can be measured. Also, similar to FIG. 1, the arrows B1, B2, B3 disposed adjacent to the motion base 212 in FIG. 2 schematically depict the displaceable nature of the force measurement assembly 202, which is effectuated by the motion base 212. Moreover, as in FIG. 1, the curved arrows R1, R2, R3 in FIG. 2 schematically illustrate the ability of the force measurement assembly 202 to be rotated about a plurality of different axes, the rotational movement of the force measurement assembly 202 being generated by the motion base 212.

While the exemplary force measurement systems 100, 200 explained above employ force measurement assemblies 102, 202 that are configured to receive a subject in an upright position, it is to be understood that the invention is not so limited. Rather, the present invention can be practiced with a force measurement assembly that accommodates a subject in a position other than an upright position, such as a supine position. One such example of a force measurement assembly that receives a subject in a supine position is a ballistocardiographic bed.

The primary components of the motion base 112, 212 are schematically depicted in FIGS. 3a and 3b. As depicted in these figures, the motion base 112, 212 comprises a movable top surface 124 that is preferably displaceable (represented by straight arrows) and rotatable (illustrated by curved arrows R1, R2) in 3-dimensional space by means of a plurality of actuators 126. In both the first and second embodiments, the force plate 106 is disposed on the movable top surface 124. The motion base 112, 212 performs several functions in the force measurement system. First, the motion base 112, 212 is used for the dynamic testing of subjects when, for example, the subject is being tested in a virtual reality environment. Secondly, the motion base 112, 212 is used during the calibration procedure of the force measurement systems 100, 200 in order to generate applied linear and/or rotational motion profiles that are applied to the force measurement assemblies 102, 202 so that the inertial parameters of the force measurement assembly 102, 202 can be determined. While the motion base 112, 212 is preferably displaceable and rotatable in 3-dimensional space, it is to be understood that the present invention is not so limited. Rather, motion bases 112, 212 that only are capable of 1 or 2 dimensional motion could be provided without departing from the spirit and the scope of the claimed invention. Also, motion bases 112, 212 that are only capable of either linear motion or rotational motion are encompassed by the present invention.

In FIGS. 4a and 4b, an accelerometer 128 and an angular velocity sensor 130 are schematically depicted on a force measurement assembly 102. While the exemplary force measurement assembly 102 depicted in FIGS. 4a and 4b more closely resembles that of the first embodiment, it is to be understood that FIGS. 4a and 4b are equally applicable to the second embodiment of the invention, wherein the force measurement assembly 202 includes a treadmill 204. As described above, the force plate 106 is disposed below the top surface 206 of the treadmill 204 so that the load being applied by the subject disposed on the top surface 206 can be determined. As shown in FIGS. 4a and 4b, the force plate 106 comprises a top plate 132 supported on a plurality of force transducers 134. While a total of four (4) force transducers 134 are depicted in FIGS. 4a and 4b (i.e., one force transducer 134 being located near each corner of the top plate 132, one of ordinary skill in the art will appreciate that a different quantity of force transducers may be used (i.e., more than four or less than four) without departing from the spirit and scope of the claimed invention. In these figures, an accelerometer 128 and an angular velocity sensor 130 are shown spaced apart internally within the top plate 132. Although, it is to be understood that the placement of the accelerometer 128 and the angular velocity sensor 130 is not limited to any particular location on the top plate 132 of the force plate 106. Rather, the accelerometer 128 and the angular velocity sensor 130 can be placed virtually anywhere on the force plate 106.

FIGS. 5a and 5b are similar in most respects to FIGS. 4a and 4b described above, except that a plurality of accelerometers 128 are depicted, rather than a single accelerometer 128, as well as a plurality of angular velocity sensors 130. In particular, the exemplary embodiment of FIGS. 5a and 5b depicts three accelerometers 128 being provided with two angular velocity sensors 130. However, as described above with regard to FIGS. 4a and 4b, the invention is in no way limited to the specific quantity of devices 128, 130 depicted in FIGS. 5a and 5b. Rather, one of ordinary skill in the art will appreciate that varying the quantities of accelerometers 128 and angular velocity sensors 130 are encompassed by the claimed invention. Moreover, as explained above with respect to FIGS. 4a and 4b, the placement of each accelerometer 128 and angular velocity sensor 130 is not limited to any particular location within the top plate 132 of the force plate 106, rather the location of the devices 128, 130 can be varied.

Figure 6B:
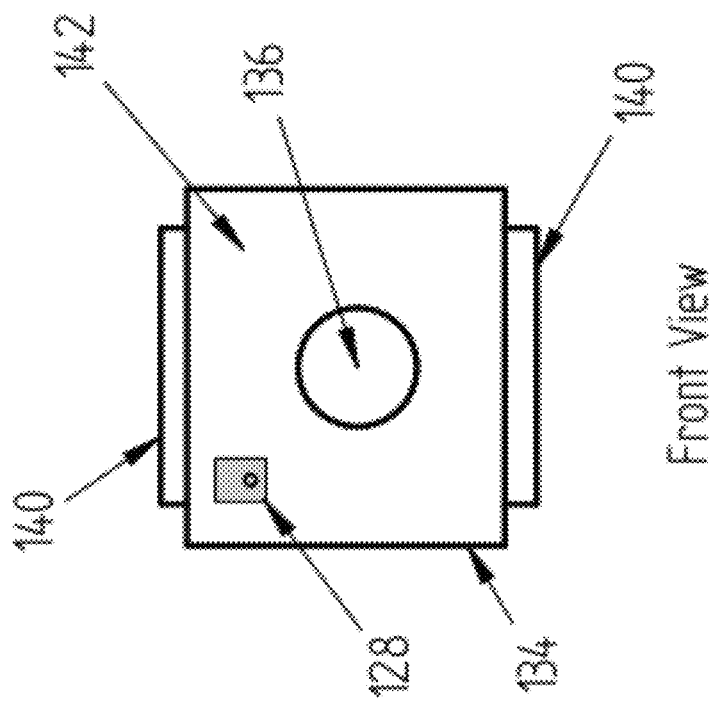
FIG. 6b is a schematic front view of a force transducer with the location of an accelerometer depicted thereon according to an embodiment of the invention.
Figure 6A:
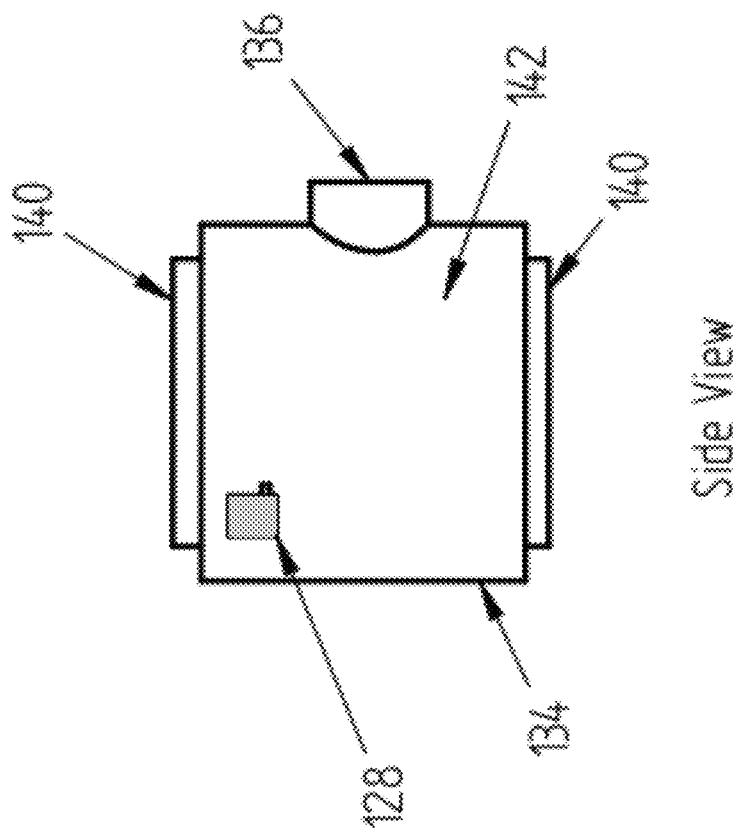
FIG. 6a is a schematic side view of a force transducer with the location of an accelerometer depicted thereon according to an embodiment of the invention.

FIGS. 6a and 6b schematically represent a force transducer 134 having an accelerometer 128 disposed thereon. While the force transducer 134 depicted in FIGS. 6a and 6b is a pylon-type transducer, which has a generally cylindrical shape, one of ordinary skill in the art will appreciate that the present invention can be practiced with other types of force transducers such as, but not limited to, beam-type force transducers. In the exemplary embodiments depicted in FIGS. 4a-4b and 5a-5b, each force transducer 134 is disposed between the bottom surface of the top plate 132 and the top surface of the motion base 112. As shown in FIGS. 6a and 6b, the force transducer 134 has a force transducer sensing element 140 disposed on the top and bottom of a cylindrical casing 142. Also, as depicted in these figures, an electrical connector 136 is disposed on one side of the cylindrical casing 142. The electrical connector 136 is operatively connected to one or more wires that transmit the output signal of the force transducer sensing elements 140 to a signal amplifier/converter and/or data acquisition/data processing device 104. Moreover, as described above for accelerometer(s) being mounted on the top plate 132, the quantity of accelerometers 128, and the location of each accelerometer 128, can be varied from that which is depicted in the exemplary embodiment of FIGS. 6a and 6b. Also, although not explicitly shown, the force transducer 134 can be provided with one or more angular velocity sensors 130 disposed thereon or therein.

FIGS. 7a and 7b are similar to FIGS. 6a and 6b described above, except that a plurality of accelerometers 128 are depicted, rather than a single accelerometer 128. Also, a plurality of angular velocity sensors 130 are shown on the force transducer 134. In particular, the exemplary embodiment of FIGS. 7a and 7b depicts three accelerometers 128 being provided with two angular velocity sensors 130. However, as described above with regard to FIGS. 5a-5b and 6a-6b, the invention is in no way limited to the specific quantity of devices 128, 130 depicted in FIGS. 7a and 7b. Rather, one of ordinary skill in the art will appreciate that varying quantities of accelerometers 128 and angular velocity sensors 130 are encompassed by the claimed invention. Moreover, the placement of each accelerometer 128 and each angular velocity sensor 130 is not limited to any particular location on the force transducer 134, rather the location of the devices 128, 130 can be varied.

Figure 8:
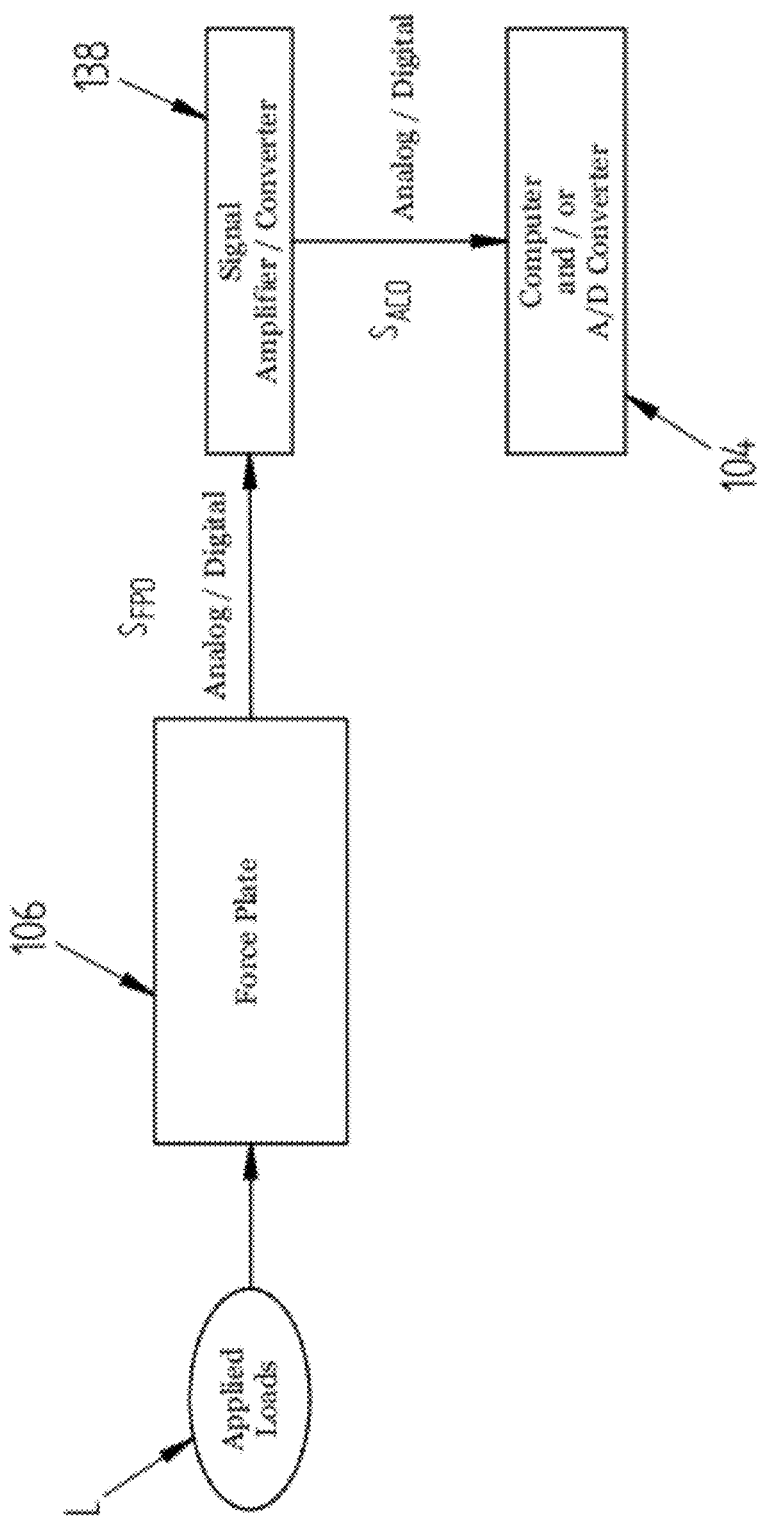
FIG. 8 is a block diagram illustrating the data acquisition/data processing system according to an embodiment of the invention.

FIG. 8 graphically illustrates the acquisition and processing of the load data carried out by the force measurement systems 100, 200. Initially, as shown in FIG. 8, a load L is applied to the force plate 106 by a subject disposed thereon. After which, the force plate 106 transmits a force plate output signal $S_{FPO}$ to a signal amplifier/converter 138. Depending on the hardware that is employed, the force plate output signal $S_{FPO}$ can be either in the form of an analog signal or a digital signal. The signal amplifier/converter 138 magnifies the force plate output signal $S_{FPO}$, and if the signal $S_{FPO}$ is of the analog-type, it may also convert the analog signal to a digital signal. Then, the signal amplifier/converter 138 transmits either a digital or analog signal $S_{ACO}$, to a data acquisition/data processing device 104. In addition to a computer, which generally includes a central processing unit (CPU) 114, graphical user interface 118, and a plurality of user input devices 116, 120, the data acquisition/data processing device 104 may further comprise an analog-to-digital (A/D) converter if the signal $S_{ACO}$ is in the form of an analog signal. In such a case, the analog-to-digital converter will convert the analog signal into a digital signal for processing by a central processing unit 114.

Now, the inertial compensation system of the present invention will be described in detail. Advantageously, in a preferred embodiment, the inertial compensation system of the present invention employs a calibration procedure that empirically determines the inertial parameters of the force measurement assembly 102, 202 using applied linear and/or rotational motion profiles executed by the motion base 112, 212 of the force measurement system 100, 200. In particular, the motion base 112, 212 is programmed in order to displace the force measurement assembly using a set of applied motion profiles. The calibration procedure described hereinafter is particularly well suited to large force measurement systems that undergo complex motions such as, but not limited to, instrumented treadmill systems. The procedure also produces accurate results for measurement systems wherein the entire system is moving. There are no assumptions made about the system, rather the procedure utilizes three-dimensional (3D) equations of motion such that every inertial parameter is identified by the calibration procedure. In a preferred embodiment of the invention, the calibration procedure is embodied in a computer-readable medium loaded on the data acquisition/data processing device 114.

Figure 9:
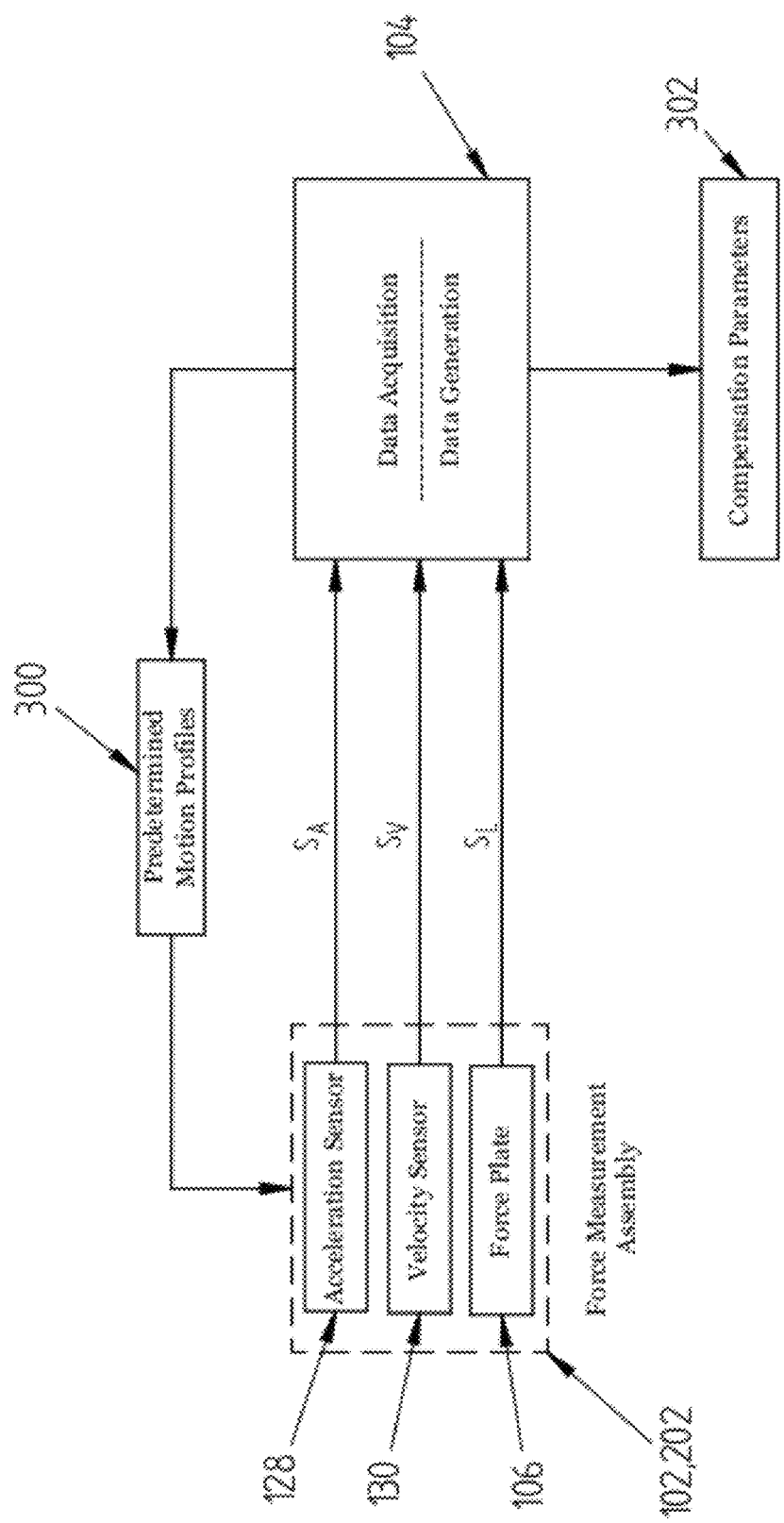
FIG. 9 is a block diagram illustrating the calibration routine according to an embodiment of the invention.

In FIG. 9, the calibration procedure of the force measurement systems 100, 200 is graphically depicted. Initially, the central processing device 114 of the data acquisition/data processing device 104 executes a calibration procedure stored on a computer-readable medium. At the beginning of the calibration procedure, a plurality of applied motion profiles 300 are applied to the force measurement assembly 102, 202. While the force measurement assembly 102, 202 is being subjected to the applied motion profiles 300, signals $S_A$, $S_V$, and $S_L$ from the acceleration sensor 128, angular velocity sensor 130, and force plate 106, respectively, are transmitted to the data acquisition/data processing device 104 so that these signals $S_A$, $S_V$, and $S_L$ can undergo processing. Signals $S_A$, $S_V$, and $S_L$ are collected while the force measurement assembly 102, 202 is subjected to a plurality of different, applied motion profiles. After each applied motion profile 300 is executed, the values of the compensation parameters 302 are determined.

In a preferred embodiment, the applied motion profiles 300 are sinusoidal and/or sawtooth waveforms generated by the motion base 112, 212. A variety of different motion profiles can be utilized for effectively calibrating the force measurement systems 100, 200. However, if the motion base 112, 212 is used to generate the motion profiles 300, the amplitudes and the frequencies of the waveforms that are used for the calibration procedure are limited to that which is capable of being produced by the motion base 112, 212. Although, it is to be understood that, as an alternative to using the motion base 112, 212, the applied motion profiles 300 may be applied to the force measurement assembly 102, 202 by utilizing another device or by the manual application thereof.

In order to better illustrate the calibration procedure summarized above, the mathematical calculations carried out by the data acquisition/data processing device 104 will be explained. The equations that describe the force inertia relationship for the moving force measurement assemblies 102, 202 are as follows:

$$m \cdot \vec{a}_G = \vec{F}_m + \vec{F}_e \quad (1)$$

$$J\vec{\omega} + \vec{\omega} \times J\vec{\omega} = \vec{M}_m + \vec{M}_e + \vec{r}_G \times (\vec{F}_m + \vec{F}_e) \quad (2)$$

where:
m: mass of the system inertia measured by the transducer
$\vec{a}_G$: acceleration of mass m
$\vec{F}_m$: measured forces from the transducer
$\vec{F}_e$: externally applied forces
J̌: rotational inertia of the system
$\vec{\omega}$: angular acceleration of the system $\vec{M}_e$: angular velocity of the system
$\vec{M}_m$: measured moments from the transducer
$\vec{M}_e$: externally applied moments
$\vec{r}_G$: position vector of the center of gravity.

As equations (1) and (2) clearly illustrate, the measured forces $\vec{F}_m$ and moments $\vec{M}_m$ are mathematically distinct from the externally applied forces $\vec{F}_e$ and moments $\vec{M}_e$. The load output (i.e., forces $\vec{F}_m$ and moments $\vec{M}_m$) of the force measurement assembly 102, 202 is measured using the force transducers 134 with force transducer elements 140 disposed thereon. In a preferred embodiment of the invention, compensating for the inertia loads of the force measurement assembly 102, 202 requires independent measurement of the accelerations and angular velocities experienced thereby. These measurements are capable of being performed using commercially available accelerometers and angular velocity sensors (rate gyroscopes). In the preferred embodiment, three 3-component linear accelerometers and a 3-component angular velocity sensor (rate gyroscope) are used to measure the kinematics (e.g., parameters $\vec{a}_G$ and $\vec{\omega}$) of the force measurement assembly 102, 202. The equations that describe the kinematics of the force measurement assembly 102, 202 using the accelerometers at three (3) non-collinear points $P_1$, $P_2$, $P_3$ and center of mass G are as follows:

$$\vec{a}_{P1} = \vec{a}_{P2} + \vec{\omega} \times \vec{r}_{12} + \vec{\omega} \times (\vec{\omega} \times \vec{r}_{12}) \quad (3)$$

$$\vec{a}_{P2} = \vec{a}_{P3} + \vec{\omega} \times \vec{r}_{23} + \vec{\omega} \times (\vec{\omega} \times \vec{r}_{23}) \quad (4)$$

$$\vec{a}_G = \vec{a}_{P1} + \vec{\omega} \times \vec{r}_{G1} + \vec{\omega} \times (\vec{\omega} \times \vec{r}_{G1}) \quad (5)$$

where:
$\vec{a}_{P1}$, $\vec{a}_{P2}$, $\vec{a}_{P3}$: measured accelerations at points $P_1$, $P_2$ and $P_3$ respectively
$\vec{r}_{12}$, $\vec{r}_{23}$: position vectors from $P_2$ to $P_1$ and $P_3$ to $P_2$ respectively
$\vec{r}_{G1}$: position vector from point $P_1$ to mass center G.

In equations (3)-(5) above, the position vectors $\vec{r}_{12}$, $\vec{r}_{23}$ are preferably determined prior to the commencement of the calibration procedure using an analytical method. For example, the position vectors $\vec{r}_{12}$, $\vec{r}_{23}$ can be determined from computerized drawings of the force measurement assembly 102, 202 by utilizing a computer-assisted design (CAD) program. Although, one of ordinary skill in the art will appreciate that the position vectors $\vec{r}_{12}$, $\vec{r}_{23}$ can also be determined using other methods without departing from the spirit and the scope of the invention.

Measurement system constants (compensation parameters 302), such as mass m, rotational inertia J̌, and geometric parameters of the system are needed in order to solve equations (1) and (2) above. These parameters are determined by subjecting the force measurement assembly 102, 202 to a plurality of applied motion profiles 300 such that, after each motion profile is executed, the values of the system constants are determined. In a preferred embodiment, an unloaded force measurement assembly 102, 202 initially is displaced using a linear acceleration profile in order to simplify the mathematical determination of the mass m. Because both $\vec{F}_e=0$ and $\vec{M}_e=0$ for the unloaded force measurement assembly 102, 202, the mass m can be determined using equation (1). Moreover, because the angular velocity $\vec{\omega}$ and the angular acceleration $\vec{\omega}$ are both equal to zero when the unloaded force measurement assembly 102, 202 is subjected to only a linear acceleration, the position vector of the center of gravity $\vec{r}_G$ can be computed from equation (2), wherein the term $\vec{J}\vec{\omega}+\vec{\omega}\times\vec{J}\vec{\omega}$ is equal to zero and drops out of equation (2). Then, different motion profiles involving angular accelerations and angular velocities are applied to the force measurement assembly 102, 202 so that the angular acceleration $\vec{\omega}$ can be solved from the over-determined set of equations (3) and (4) by using the accelerations measured by the three accelerometers and the angular velocity $\vec{\omega}$ measured by the angular velocity sensor (rate gyroscope). Finally, the elements of the rotational inertia matrix J can be solved using equation (2). By following the aforementioned procedural steps, all of the inertial and geometric constants of the force measurement assembly 102, 202 can be determined.

While a linear acceleration profile is used for the displacement of the unloaded force measurement assembly 102, 202 in the preferred embodiment so as to facilitate the computational determination of the mass m, it is to be understood that the present invention is not so limited. Rather, a non-linear acceleration profile can be applied to unloaded force measurement assembly 102, 202. In such a case, rather than simply using equation (1), the mass m will be determined along with the other measurement system constants by simultaneously solving equations (1) and (2) and using the mathematical relationships set forth in equations (3)-(5).

Figure 10:
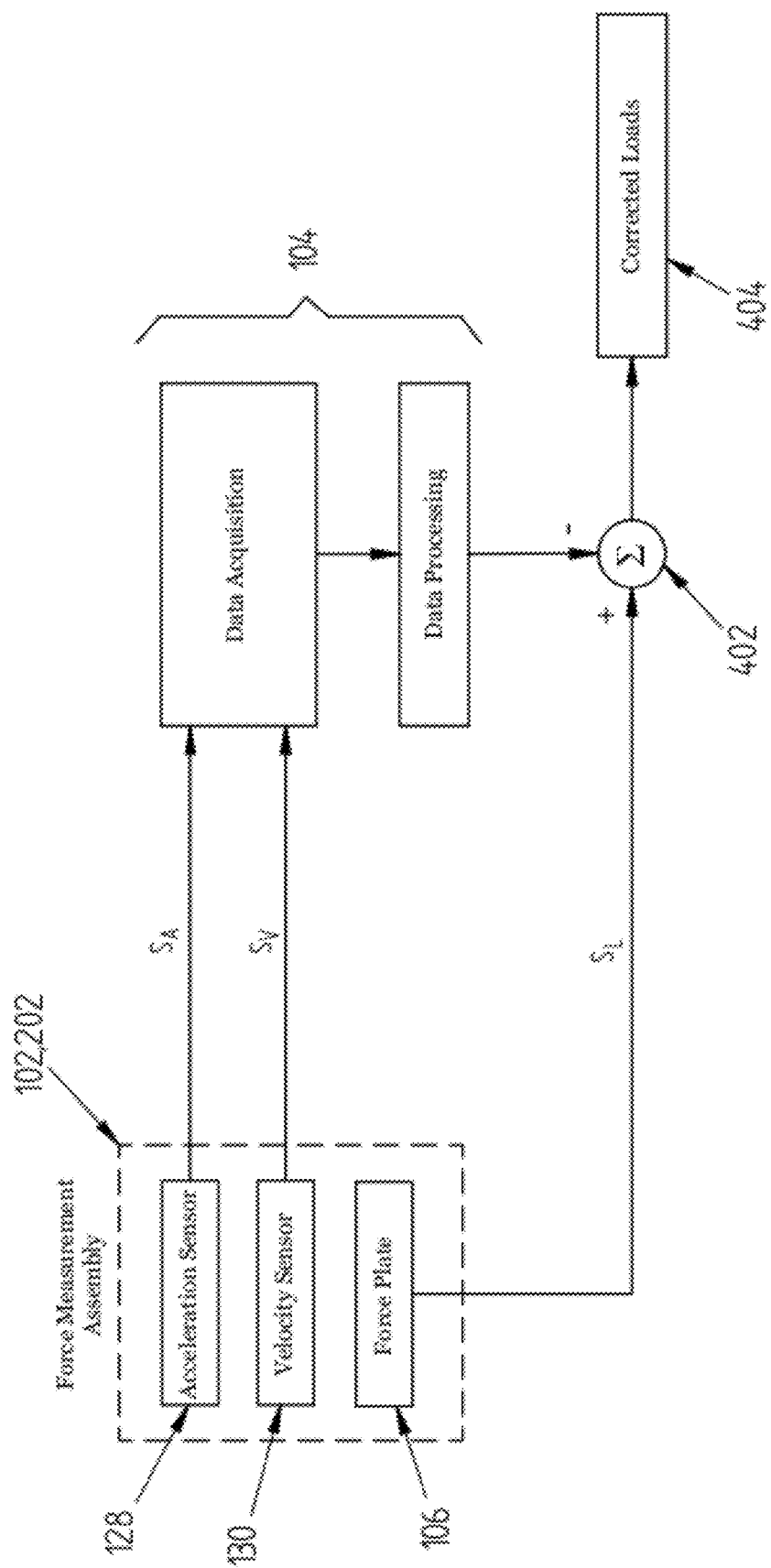
FIG. 10 is a block diagram illustrating the compensation procedure according to an embodiment of the invention.

The inertial compensation procedure of the force measurement systems 100, 200 is graphically depicted in FIG. 10. After the calibration procedure described above has been performed, the signals $S_A$ and $S_V$ from the acceleration sensor 128 and angular velocity sensor 130, respectively, are fed into the data acquisition/data processing device 104 and mathematically combined with the values of the compensation parameters determined during the calibration procedure. Then, the load signals $S_L$ from the force transducers of the force plate 106 are mathematically combined with the computed forces due to the inertia of the system at 402. Once the load signals $S_L$ have been combined with the computed inertia forces, a corrected load output 404 is obtained.

Now, to further explain the inertial compensation procedure summarized above, the mathematical manipulations carried out by the data acquisition/data processing device 104 will be explained. During the inertial calibration procedure, the mass m, the rotational inertia J, and at least one geometric parameter (e.g., the position of the center of mass $\vec{r}_G$) of the force measurement assembly 102, 202 were determined. These inertial parameters (m, and the geometric parameters) are used in conjunction with the signals $S_A$ and $S_V$ from the acceleration sensor 128 and the angular velocity sensor 130, and load signals $S_L$ from the force transducers 134, of the force plate 106 in order to compute the desired externally applied forces $\vec{F}_e$ and moments $\vec{M}_e$ using the following two equations:

$$\vec{F}_e = m \cdot \vec{a}_G - \vec{F}_m \quad (6)$$

$$\vec{M}_e = \vec{J}\vec{\omega} + \vec{\omega}\times\vec{J}\vec{\omega} - \vec{M}_m - \vec{r}_G \times (\vec{F}_m + \vec{F}_e) \quad (7)$$

Equations (6) and (7) are similar to equations (1) and (2) discussed above, except that the terms in these two equations have been rearranged in order to solve for the desired externally applied forces $\vec{F}_e$ and moments $\vec{M}_e$. Inertia compensation of the load measurement requires using the parameters $\vec{r}_G$, $\vec{\omega}$, and $\vec{\omega}$ together with equations (3), (4), and (5), and the load output of the force transducers 134, such that the externally applied forces $\vec{F}_e$ and moments $\vec{M}_e$ can be computed using equations (6) and (7). Because all of the fixed system parameters, such as the mass m and the rotational inertia matrix J, are computed in the inertial calibration stage, the unknown externally applied loads $\vec{F}_e$ and $\vec{M}_e$ can be solved using equations (6) and (7). Thus, after the above described mathematical manipulations have been performed, the unwanted inertial effect of the force measurement assembly 102, 202 has been eliminated from the output load determined by the force measurement systems 100, 200.

Although the invention has been shown and described with respect to a certain embodiment or embodiments, it is apparent that this invention can be embodied in many different forms and that many other modifications and variations are possible without departing from the spirit and scope of this invention. For example, rather than using three 3-component accelerometers, a total of nine single-component accelerometers could be used for determining the accelerations of the force measurement assemblies 102, 202. Similarly, three single-component angular velocity sensors (rate gyroscopes) could be substituted for the single 3-component angular velocity sensor that is used in the preferred embodiment described above.

While exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A force measurement system having inertial compensation, the force measurement system comprising:
    a force measurement assembly configured to receive a subject, the force measurement assembly including:
        a surface for receiving at least one portion of the body of the subject;
        at least one force transducer, the at least one force transducer configured to sense a measured quantity and output a signal that is representative of forces and/or moments being applied to the surface of the force measurement assembly by the subject;
        at least one accelerometer configured to measure the acceleration of the force measurement assembly;
        at least one angular velocity sensor configured to measure the angular velocity of the force measurement assembly; and
    a data processing device operatively coupled to the force measurement assembly, the data processing device configured to receive the signal that is representative of the forces and/or moments being applied to the surface of the force measurement assembly by the subject and to convert the signal into output forces and/or moments, the data processing device being configured to receive the acceleration and the angular velocity measured by the at least one accelerometer and the at least one angular velocity sensor, respectively, and the data processing device further being configured to use the acceleration and the angular velocity measured by the at least one accelerometer and the at least one angular velocity sensor, respectively, to compute inertial forces and moments, and to determine corrected externally applied forces by computing the mathematical difference between the computed inertial forces and the output forces, and/or to determine corrected externally applied moments by computing the mathematical difference between the computed inertial moments and the output moments so as to improve the measurement accuracy of the forces and/or moments being applied to the surface of the force measurement assembly by the subject;

wherein the data processing device executes a calibration procedure, which is loaded thereon from a computer-readable medium, and determines inertial parameters of the force measurement assembly through the utilization of linear and/or rotational motion profiles applied to the force measurement assembly by a motion base disposed thereunder; and wherein the inertial parameters of the force measurement assembly comprise the mass of the assembly, the rotational inertia of the assembly, and the position vector of the center of gravity of the assembly, and wherein the mass of the assembly is computed as a function of measured forces determined using the at least one force transducer and the acceleration measured by the at least one accelerometer.

2. The force measurement system according to claim 1, wherein the data processing device computes the inertial moments as a function of the angular velocity measured by the at least one angular velocity sensor, as a function of an angular acceleration of the force measurement assembly, and as a function of the rotational inertia of the assembly in the form of an inertia matrix that is determined during the calibration procedure.

3. The force measurement system according to claim 2, wherein the data processing device computes the angular acceleration of the force measurement assembly by solving a plurality of kinematic equations using the acceleration and the angular velocity measured by the at least one accelerometer and the at least one angular velocity sensor, respectively.

4. The force measurement system according to claim 1, wherein the at least one angular velocity sensor comprises a multi-component angular velocity sensor that is capable of measuring angular velocities of the force measurement assembly about multiple rotational axes.

5. The force measurement system according to claim 4, wherein the data processing device computes the inertial moments as a function of the angular velocities measured by the multi-component angular velocity sensor, as a function of an angular acceleration of the force measurement assembly, and as a function of the rotational inertia of the assembly in the form of an inertia matrix that is determined during the calibration procedure.

6. The force measurement system according to claim 1, wherein the at least one force transducer comprises a plurality of force transducers for sensing measured quantities that are representative of multi-dimensional forces and moments being applied to the surface of the force measurement assembly by the subject.

7. The force measurement system according to claim 6, wherein the at least one accelerometer comprises a plurality of accelerometers so as to enable multi-axis acceleration of the force measurement assembly to be determined, thereby compensating for the movement of the force measurement assembly in more than one direction.

8. The force measurement system according to claim 1, wherein the force measurement assembly is in the form of a force plate or platform.

9. The force measurement system according to claim 1, wherein the force measurement assembly is in the form of an instrumented treadmill.

10. A force measurement system having inertial compensation, the force measurement system comprising:

a force measurement assembly configured to receive a subject, the force measurement assembly including:
  a surface for receiving at least one portion of the body of the subject;
  at least one force transducer, the at least one force transducer configured to sense a measured quantity and output a signal that is representative of forces and/or moments being applied to the surface of the force measurement assembly by the subject;
  at least one accelerometer configured to measure the acceleration of the force measurement assembly; and
a data processing device operatively coupled to the at least one force transducer and the at least one accelerometer of the force measurement assembly, the data processing device being configured to execute a calibration procedure that is loaded thereon from a computer-readable medium, and to determine inertial parameters of the force measurement assembly, which include the mass of the force measurement assembly, by utilizing the measured acceleration of the force measurement assembly while a plurality of linear and/or rotational motion profiles are applied to the force measurement assembly by a motion generating source external thereto;

wherein the data processing device is configured to receive the signal that is representative of the forces and/or moments being applied to the surface of the force measurement assembly by the subject, and to convert the signal into output forces and/or moments, the data processing device further being configured to compute the mass of the force measurement assembly as a function of measured forces determined using the at least one force transducer and the acceleration measured by the at least one accelerometer; and wherein the data processing device is further configured to utilize the determined inertial parameters of the force measurement assembly, which include the mass of the force measurement assembly, and the acceleration measured by the at least one accelerometer for correcting the output forces and/or moments, the data processing device being configured to use the acceleration measured by the at least one accelerometer to compute inertial forces, and to determine corrected externally applied forces by computing the mathematical difference between the computed inertial forces and the output forces so as to improve the measurement accuracy of the forces and/or moments being applied to the surface of the force measurement assembly by the subject.

11. The force measurement system according to claim 10, wherein the force measurement assembly further comprises at least one angular velocity sensor configured to measure the angular velocity of the force measurement assembly.

12. The force measurement system according to claim 11, wherein the data processing device is further configured to use the angular velocity measured by the at least one angular velocity sensor to compute inertial moments, and to correct the output moments using the computed inertial moments.

13. The force measurement system according to claim 12, wherein the data processing device computes the inertial moments as a function of the angular velocity measured by the at least one angular velocity sensor, and as a function of an angular acceleration of the force measurement assembly.

14. The force measurement system according to claim 12, wherein the at least one angular velocity sensor comprises a multi-component angular velocity sensor that is capable of measuring angular velocities of the force measurement assembly about multiple rotational axes.

15. The force measurement system according to claim 14, wherein the data processing device computes the inertial moments as a function of the angular velocities measured by the multi-component angular velocity sensor, and as a function of an angular acceleration of the force measurement assembly.

16. The force measurement system according to claim 15, wherein the data processing device computes the angular acceleration of the force measurement assembly by solving a plurality of kinematic equations using the acceleration and the angular velocity measured by the at least one accelerometer and the at least one angular velocity sensor, respectively.

17. The force measurement system according to claim 10, wherein the at least one force transducer comprises a plurality of force transducers for sensing measured quantities that are representative of multi-dimensional forces and moments being applied to the surface of the force measurement assembly by the subject.

18. The force measurement system according to claim 17, wherein the at least one accelerometer comprises a plurality of accelerometers so as to enable multi-axis acceleration of the force measurement assembly to be determined, thereby compensating for the movement of the force measurement assembly in more than one direction.

19. The force measurement system according to claim 10, wherein the force measurement assembly is in the form of a force plate or platform.

20. The force measurement system according to claim 10, wherein the force measurement assembly is in the form of an instrumented treadmill.

21. The force measurement system according to claim 10, wherein the inertial parameters of the force measurement assembly further comprise the rotational inertia of the assembly and the position vector of the center of gravity of the assembly.

22. A force measurement system having inertial compensation, the force measurement system comprising:
a force measurement assembly configured to receive a subject, the force measurement assembly including:
a surface for receiving at least one portion of the body of the subject;
at least one force transducer, the at least one force transducer configured to sense a measured quantity and output a signal that is representative of forces and/or moments being applied to the surface of the force measurement assembly by the subject;
at least one linear accelerometer configured to measure a linear acceleration of the force measurement assembly;
a motion base, which includes a plurality of actuators, operatively coupled to the force measurement assembly, the motion base configured to both displace and rotate the force measurement assembly in multiple dimensions; and
a data acquisition and processing device operatively coupled to the force measurement assembly, the data acquisition and processing device configured to receive the signal that is representative of the forces and/or moments being applied to the surface of the force measurement assembly by the subject and to convert the signal into output forces and/or moments, the data acquisition and processing device being configured to receive the linear acceleration measured by the at least one linear accelerometer, and the data acquisition and processing device further being configured to use the linear acceleration measured by the at least one linear accelerometer to compute inertial forces, and to determine corrected externally applied forces by computing the mathematical difference between the computed inertial forces and the output forces so as to improve the measurement accuracy of the forces and/or moments being applied to the surface of the force measurement assembly by the subject;
wherein the data acquisition and processing device executes a calibration procedure, which is loaded thereon from a computer-readable medium, and determines inertial parameters of the force measurement assembly through the utilization of linear and/or rotational motion profiles as applied to the force measurement assembly by the motion base; and wherein the inertial parameters of the force measurement assembly include the mass of the force measurement assembly, the mass of the force measurement assembly being computed as a function of measured forces determined using the at least one force transducer and the acceleration measured by the at least one linear accelerometer.

23. The force measurement system according to claim 22, wherein the force measurement assembly further comprises at least one angular velocity sensor configured to measure the angular velocity of the force measurement assembly.

24. The force measurement system according to claim 23, wherein the data acquisition and processing device is further configured to use the angular velocity measured by the at least one angular velocity sensor to compute inertial moments, and the data acquisition and processing device is configured to determine corrected externally applied moments by computing the mathematical difference between the computed inertial moments and the output moments, so as to improve the measurement accuracy of the moments being applied to the surface of the force measurement assembly by the subject.

25. The force measurement system according to claim 24, wherein the data acquisition and processing device computes the inertial moments as a function of the angular velocity measured by the at least one angular velocity sensor, and as a function of an angular acceleration of the force measurement assembly.

26. The force measurement system according to claim 25, wherein the data acquisition and processing device computes the angular acceleration of the force measurement assembly by solving a plurality of kinematic equations using the acceleration and the angular velocity measured by the at least one linear accelerometer and the at least one angular velocity sensor, respectively.

27. The force measurement system according to claim 22, wherein the at least one force transducer comprises a plurality of force transducers for sensing measured quantities that are representative of multi-dimensional forces and moments being applied to the surface of the force measurement assembly by the subject.

28. The force measurement system according to claim 27, wherein the at least one accelerometer comprises a plurality of accelerometers so as to enable multi-axis acceleration of the force measurement assembly to be determined, thereby compensating for the movement of the force measurement assembly in more than one direction.

29. The force measurement system according to claim 22, wherein the force measurement assembly is in the form of a force plate or platform.

30. The force measurement system according to claim 22, wherein the force measurement assembly is in the form of an instrumented treadmill.

* * * * *